United States Patent [19]

Tiep

[11] 4,063,550
[45] Dec. 20, 1977

[54] METHOD AND APPARATUS FOR TREATING BRONCHIAL ASTHMA

[76] Inventor: Brian L. Tiep, 632 Norumbega Drive, Monrovia, Calif. 91016

[21] Appl. No.: 690,850

[22] Filed: May 28, 1976

[51] Int. Cl.² ............................................. A61B 5/00
[52] U.S. Cl. .................................. 128/2 R; 128/2 K; 35/22 R
[58] Field of Search .......... 128/2 R, 2 K, 1 R, 2.05 S, 128/2.1 B; 35/22 R, 17

[56] References Cited

U.S. PATENT DOCUMENTS

| 2,705,742 | 4/1955 | Miller | 128/2 R |
| 2,934,060 | 4/1960 | Satter | 128/1 R |
| 3,368,551 | 2/1968 | Hardyck | 128/2 R |
| 3,566,858 | 3/1971 | Larson | 128/1 R |
| 3,742,935 | 7/1973 | Baessler et al. | 128/2 K X |
| 3,882,850 | 5/1975 | Bailin et al. | 128/2.1 B |
| 3,895,316 | 7/1975 | Fein | 128/2.05 S |

FOREIGN PATENT DOCUMENTS

| 867,656 | 5/1961 | United Kingdom | 128/1 R |

OTHER PUBLICATIONS

Fried, "Biofeedback:Teaching Your Body to Heal Itself", Reader's Digest, May 1974, pp. 110-113.
Waite, "Alpha Brain Waves & Biofeedback Training", Popular Electronics, Dec. 1972, pp. 33-38.

Primary Examiner—Wm. E. Kamm
Assistant Examiner—Lee S. Cohen

[57] ABSTRACT

An individual suffering from bronchial asthma can be trained to relax his or her bronchial muscles in order to facilitate breathing. In such training a microphone is located adjacent to the trachea of the individual and is utilized to provide a signal. This signal may be directly amplified and converted to an audible sound through the use of a speaker, but it is preferably utilized to provide a variable frequency signal corresponding to the amplitude of the signal from the microphone, and this latter signal is supplied to the speaker to provide a variable tone. This tonal variation effectively indicates to an individual the manner in which the individual is breathing. Such an individual can learn to control his or her breathing in such a manner as to regulate the frequency of the tone produced by the speaker so that the sound produced corresponds to the bronchial muscles being relaxed.

4 Claims, 1 Drawing Figure

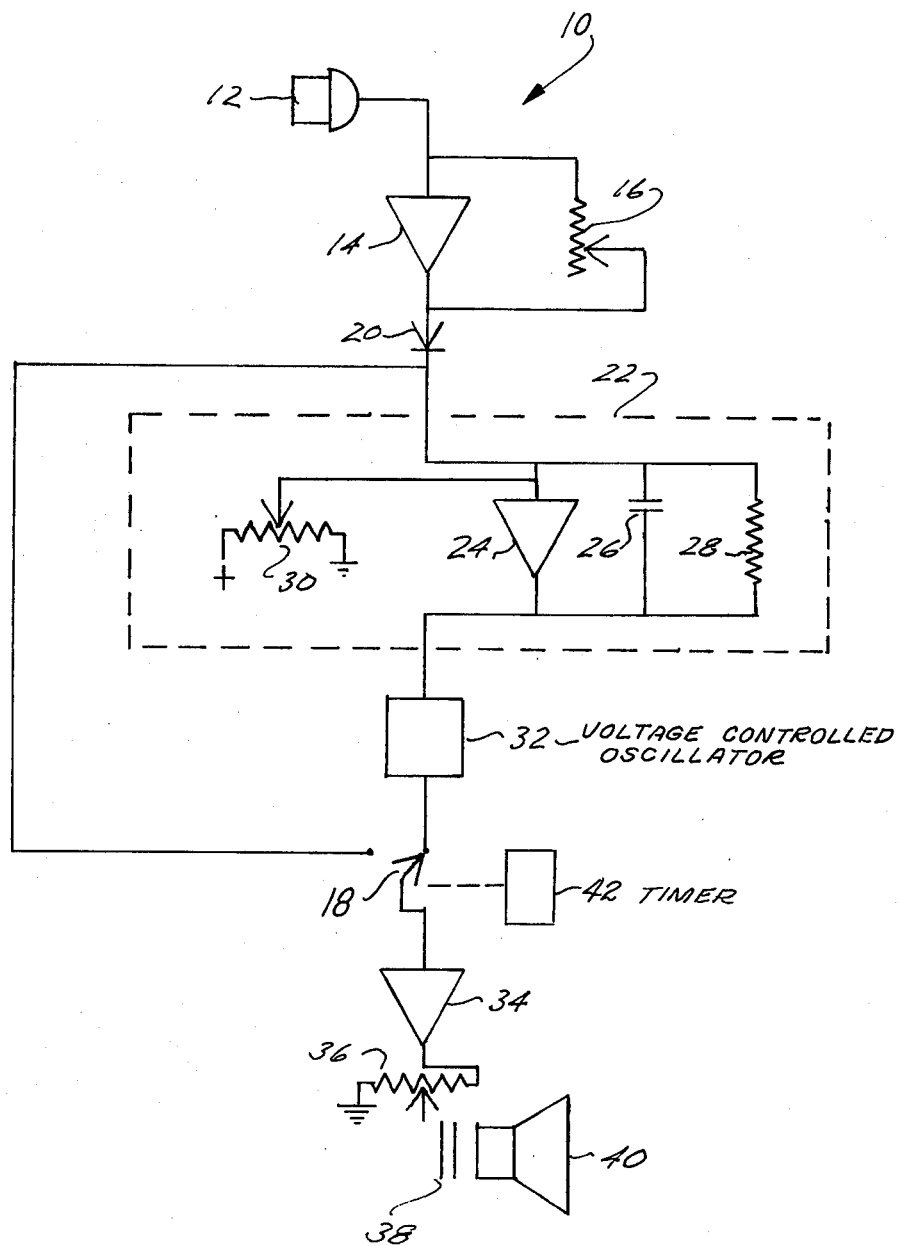

METHOD AND APPARATUS FOR TREATING BRONCHIAL ASTHMA

CROSS-REFERENCE TO RELATED APPLICATIONS

The subject matter of this application is to a degree related to subject matter disclosed and claimed in the co-pending application by the inventor named herein, Brian L. Tiep, entitled "INTRATHORACIC PRESSURE BIOFEEDBACK METHOD AND APPARATUS", Ser. No. 690,851, filed 5/28/76.

BACKGROUND OF THE INVENTION

The invention set forth in this specification pertains to a new and improved method and apparatus for treating bronchial asthma through what may be referred to as a "biofeedback" type technique.

An understanding of the present invention is not considered to require a detailed knowledge of the nature of bronchial asthma or of problems associated with the ailment. However, an understanding of the invention is considered to require knowledge of the fact that a patient suffering from bronchial asthma difficulty in breathing and that this difficulty is evidenced by sounds caused by the passage of air through the bronchial passages. Generally speaking, what may be referred to as the noise level of the breathing process of a person suffering from bronchial asthma is related to the amount various bronchial muscles are "tensed up" so as to tend to constrict the breathing passages. An individual suffering from bronchial asthma will normally tend to tighten the muscles controlling the dimensions of the bronchial passages as a sort of involuntary reaction to the individual's difficulty in breathing.

It has been recognized that such an individual can breathe more easily if these muscles can be relaxed so as to permit a widening or enlargement of the various air passages in the body. There have, of course, been appropriate efforts to facilitate an individual suffering from bronchial asthma breathing through the use of appropriate medicants serving to relax the muscles controlling the dimensions of the bronchial passages. For reasons which are unimportant to an understanding of the invention it is considered preferable to enable an asthmatic patient to breathe in a desired or more or less normal manner without the use of such agents. Several different techniques have been proposed and used to various extents for this purpose.

One of such techniques requires a person suffering from bronchial asthma to go through forced expiratory maneuvers. The amount of gas exhaled during such a maneuver is measured utilizing a flow meter and the information obtained from such a meter is given to the patient as a means of instructing the patient as to the way the patient should breathe. Unfortunately this technique has the disadvantage that it does not accurately correspond to the way a person normally breathes. On occasion this technique is disadvantageous because it will tend to trigger an asthma attack.

Another technique or manner for teaching a person how to control bronchial asthma without the use of a medicant has involved what is referred to as a "body plethysmograph" (or body box). Such a device is utilized in connection with an on-line computer in order to measure airway resistance. This type of device is rather undesirable because of its size and complexity. In addition it is relatively expensive to utilize this type of structure.

As a result of these factors it is considered that there is a need for a new and improved manner of instructing an individual suffering from bronchial asthma as to a desired manner of relaxing the muscles controlling the bronchial passages so as to facilitate effective utilization of the bronchial passages. More specifically it is considered that there is a need for both for such a method and for an apparatus for use in practicing the method which is of such a character that it may be easily and conveniently constructed at a nominal cost and may be used conveniently without constant medical supervision with a minimum of difficulty.

BRIEF SUMMARY OF THE INVENTION

A broad object of the present invention is to provide a new and improved method and apparatus for treating bronchial asthma. The invention is intended to fulfill or satisfy the needs for improvement in this field specifically indicated in the preceding discussion. In its more detailed aspects the invention is concerned with providing a method ot the type indicated which may be easily and conveniently practiced with a minimum of difficulty at a comparatively nominal cost and which is extremely effective for its intended purpose. The invention is also intended to provide an apparatus for the purpose noted which may be easily and conveniently constructed at a comparatively nominal cost, which may be conveniently utilized without constant medical supervision with a minimum of difficulty, and which can be readily transported from one location to another as required.

An apparatus of this invention for use in teaching an asthmatic patient to control his or her breathing comprises: a microphone means adapted to be located adjacent to the trachea of the patient for receiving sound corresponding to the breathing of the patient, a means for providing a variable frequency response in accordance with the amplitude of the signal from the microphone means, this means of providing a variable frequency repsonse being connected to the microphone means, and a speaker means for providing an audible response corresponding to the variable frequency responce provided by the last mentioned means.

With a structure of this type the speaker provides a variable tone which corresponds in its variation to the variation in the sound picked up by the microphone means adjacent to the trachea. The patient employing the apparatus can be instructed as to the frequency of response provided by the speaker means which corresponds to what may be loosely referred to as "relaxed" breathing so that such an individual can learn to control his or her breathing in such a manner as the bronchial muscles are relaxed. The use of a variable tone which changes in pitch is considered quite desirable for the intended purpose because a normal patient can readily distinguish between changes in frequency.

BRIEF DESCRIPTION OF THE DRAWING

The invention is best more fully explained with reference to the accompanying drawing which:

The FIGURE is a diagrammatic view showing the circuit of a presently preferred apparatus in accordance with this invention.

It will be realized from a consideration of this entire specification that this specific apparatus embodies or utilizes certain principles or concepts as are discussed in this specification and as are indicated in the appended claims. Since these principles or concepts can be utilized in somewhat different manners the invention is not to be considered as being limited to the exact circuit illustrated.

DETAILED DESCRIPTION

In the drawing there is shown an apparatus 10 utilizing a conventional microphone 12 which is adapted to be located remote from the other circuit components subsequently described adjacent to the trachea of an individual. This microphone 12 may be conveniently secured in an operative location at or adjacent to the throat of an individual by any conventional, convenient manner. This microphone 12 is utilized to supply a signal, the amplitude of which corresponds to the noise produced in the bronchial passages by breathing to a conventional amplifier 14. Preferably a conventional variable resistor 16 is utilized with the amplifier 14 in order to adjust the sensitivity of the amplified signal.

The output of this amplifier 14 is supplied to one terminal of a switch 18 and to a conventional rectifying diode 20. The amplified signal passing the diode 20 is fed to a network 22 consisting of an amplifier 24, a capacitor 26, and a resistor 28, all located in parallel to one another. This entire network 22 is of a conventional or known character and may be referred to as a peak holding device serving to provide a DC voltage which corresponds to or follows the peak value of the signal obtained from the microphone 12 through the amplifier 14. This network 22 can also be referred to as a leakage integrator or enveloping circuit. Preferably it is utilized with a potentiometer 30 serving as a biasing adjustment so as to control the voltage output from this network 22.

The output from the network 22 is provided to a voltage controlled oscillator 32 of conventional design. This oscillator 32 is employed so as to provide a variable frequency which varies in accordance with the voltage provided to it from the network 22 and, of course, the latter varies in accordance with the input to the microphone 12. The output of the oscillator 32 is also supplied to the switch 18. This switch 18 is capable of being manipulated so as to supply either the output of the oscillator 32 or the output of the amplifier 14 directly to a further conventional amplifier 34. This amplifier 34 is connected through a conventional volume control 36 to a transformer 38 used to power a conventional speaker 40. Headphones may of course be substituted for the speaker 40.

The simplicity of the structure of the apparatus 10 in a sense is somewhat misleading. As the apparatus 10 is utilized in practicing the method of this invention the microphone 12 is located along the neck adjacent to the trachea so that breathing sounds will be transmitted to it. A user may then either listen to such sounds as they are amplified or may listen to a variable tone which corresponds to such sounds. Preferably as a patient-user uses the apparatus 10 the patient is instructed to assume a relaxed posture and to close his or her eyes so as to be able to effectively concentrate on the sound emitted from the speaker 40. Normally it is significantly important that the patient close his or her eyes while listening to the sound emitted by the speaker 40 because if the eyes are open there is a tendency for the individual to become distracted and to concentrate on other than the desired noise.

With the apparatus 10 the amplified sound of air passing through the bronchial passages and trachea will tend to create a sensation of concern and alarm and the patient will realize the desirability of controlling the breathing so as to minimize the amplified sound of breathing. Since the normal human ear has only somewhat limited sensitivity to small changes in sound of gradually increasing or decreasing intensity or volume directly amplified breathing sounds are not considered to provide adequate feedback to enable a patient to rapidly detect and respond to minor muscular changes as are detectable through changes in breathing noise.

The human ear is, however, relatively sensitive to comparatively restricted or limited frequency changes. Hence, when the switch 18 is in a position so that a variable tone which varies in accordance with the sound received by the microphone 12 is emitted from the speaker 40 an individual can detect even comparatively small changes in breathing patterns. This enables the individual to gradually practice body control in order to achieve increasing relaxation of the muscles controlling the bronchial passages. Such relaxation is accompanied by a gradual widening or enlarging of such passages serving to facilitate breathing. As breathing is improved in this manner there is, of course, corresponding improvement in the patient's ability to accommodate an asthmatic condition. The type of control learned in this manner will normally be usable by a patient even when the patient no longer utilizes the apparatus 10.

This technique of utilizing a variation in the frequency of a tone is considered to be more advantageous than utilizing other conventional biofeedback techniques such as a variation in a number of lights illuminated or a variation in light intensity. The use of light to "feedback" a signal to an individual is effective and can be utilized in teaching a bronchial asthma patient a proper manner of breathing but has a disadvantage in that the patient cannot effectively concentrate as effectively when his or her eyes are open as when the eyes are closed.

The use of a variable tone is in some respects analagous to the use of a tactile sensation such as is provided by a mechanical vibrator. However, the use of a variable tone is considered to be much more desirable than the use of such a tactile sensation in that no direct contact need be made with the human body. Further, the human body is not as sensitive to skin sensations such as the utilized with various types of devices directly causing a body sensation or feeling as the human ear is to extremely small changes in frequency. An apparatus of the present invention is considered quite desirable in that it utilizes a substantially immediate, direct feedback of a bodily function or operation in the form of a signal of such a character that a change in the signal —i.e., the change in the frequency— can be immediately and easily recognized.

While this alone is considered effective as an expedient for enabling an asthmatic patient to learn to control his or her breathing in order to obtain a specific tone which corresponds to the relaxation of the muscles controlling the bronchial passages a more specific concept in accordance with this invention involves teaching a patient the correlation between such a tone of a desired frequency and the actual sounds of breathing. In accordance with this invention the switch 18 may be periodically changed either by the patient or preferably by a mechanical timer 42 of conventional construction so that as the apparatus 10 is utilized the patient periodically hears his or her actual breathing sound as amplified.

By repeatedly changing back and forth so that a patient hears a tone to which the ear is quite sensitive and then hears amplified breathing sounds and then hears the tone and then the actual sound, and so on, an individual can easily develop a sensitivity enabling the individual to correlate muscle relaxation producing a tone of a desired frequency with the actual sound of breathing corresponding to the production of such a tone.

Initially in learning such correlation the actual sound of breathing should be amplified a significant extent. However, as the individual becomes more and more sensitive to the sound of breathing itself indicating a relaxation of the muscles controlling the bronchial passages the sound of breathing should be amplified a gradually decreasing extent until such time as the individual correlates a tone of a desired frequency indicating such muscle relaxation with the actual sound of breathing of his or her body which is not amplified using the apparatus 10.

It is not considered that it is practical to specify the amount that the sound of breathing should be initially amplified, the frequency at which the switch 18 should be operated so as to switch the source of the signal supplied to the speaker 40 or the duration of the periods when the switch 18 should be done in one position or another, or how gradually the actual breathing sounds should be decreased in amplification in practicing the invention. These are matters which are believed to be best adjusted in accordance with a patient's specific ability to correlate the responses noted to the sound of breathing. By teaching the method of correlation indicated it is possible for a patient to develop the ability to control his or her breathing so as to relax the muscles controlling the size of the bronchial passages even when the patient does not utilize the apparatus described.

I claim:

1. An apparatus for use in teaching an asthmatic patient to control his or her breathing so as to minimize the sound produced by the patient breathing which comprises:
   microphone means for receiving sound, said microphone means being adapted to be located adjacent to the trachea of a patient,
   means for providing a variable frequency response in accordance with an amplitude of the signal from said microphone means,
   said means for providing a variable frequency response including means for providing a DC voltage which follows the peak value of a signal from said microphone means, said means for providing a DC voltage being connected to said microphone means,
   means for varying the frequency of a signal produced by said means for providing a frequency response,
   speaker means for providing an audible response corresponding to a variable frequency response,
   voltage controlled oscillator means being connected to said means for providing a DC voltage and to said speaker means, and
   switch means permitting said speaker means to be connected to either said microphone means or to said voltage-controlled oscillator means.

2. A biofeedback method in which a body condition capable of being controlled by a person is monitored so as to provide an output indication of said condition which is capable of being sensed by the person so that the person in sensing the body condition at any specific time can control the body condition a accordance with the output indication, in which said body condition is bronchial asthma, the method comprising the steps of:
   monitoring said bronchial asthma condition by locating a microphone adjacent to the trachea of said person,
   providing a variable frequency tone which varies in accordance with changes in the noise picked up by said microphone, said variable frequency tone constituting said output indication, and
   controlling the bronchial muscles of the person by the person in accordance with changes in the frequency of said tone so as to relax his or her bronchial muscles.

3. A method as claimed in claim 2 wherein:
   said noise reaching said microphone is alternately amplified so as to be heard by said person and to provide said variable frequency tone.

4. A method as claimed in claim 3 wherein:
   the amount said noise is amplified so as to be heard by said person is gradually decreased as the person becomes able to associate a tone of a specific frequency with muscle control sufficient to accomplish relaxation of the muscles controlling the bronchial passages.

* * * * *